United States Patent [19]

Ueno et al.

[11] Patent Number: 4,869,270

[45] Date of Patent: Sep. 26, 1989

[54] CONDOM

[75] Inventors: Ryuzo Ueno; Ryuji Ueno, both of Hyogo, Japan

[73] Assignee: Kabushikikaisha Ueno Seiyaku Oyo Kenkyujo, Osaka, Japan

[21] Appl. No.: 196,574

[22] Filed: May 20, 1988

[30] Foreign Application Priority Data

May 20, 1987 [JP] Japan ................. 62-122734

[51] Int. Cl.$^4$ .............................................. A61F 5/44
[52] U.S. Cl. ....................... 128/844; 604/349
[58] Field of Search ................. 128/830, 842, 844; 604/347–353; 514/841–843

[56] References Cited

U.S. PATENT DOCUMENTS

| | | | |
|---|---|---|---|
| 3,363,624 | 1/1968 | Fishman | 128/844 |
| 4,004,591 | 1/1977 | Freimark | 604/330 |
| 4,119,094 | 10/1978 | Micklus et al. | |
| 4,446,860 | 5/1984 | Gutnick | 128/844 |
| 4,465,666 | 8/1984 | Lukas et al. | 424/78 |
| 4,663,233 | 5/1987 | Beavers | |
| 4,716,224 | 12/1987 | Sakurai et al. | 536/55.1 |
| 4,736,024 | 4/1988 | Della Valle et al. | 536/18.7 |
| 4,795,425 | 1/1989 | Pugh | 604/349 |

FOREIGN PATENT DOCUMENTS

| | | |
|---|---|---|
| 1262583 | 3/1983 | Australia . |
| 1263183 | 3/1983 | Australia . |
| 0094924 | 11/1983 | European Pat. Off. . |
| 47-283 | 9/1973 | Japan . |
| 129055 | 10/1980 | Japan . |
| 9181983 | 1/1983 | Japan . |
| 1268637 | 3/1972 | United Kingdom . |

*Primary Examiner*—C. Fred Rosenbaum
*Assistant Examiner*—Mario Costantino
*Attorney, Agent, or Firm*—Sughrue, Mion, Zinn, Macpeak & Seas

[57] ABSTRACT

A condom having a coating of thick material comprising a polysaccharide selected from the group consisting of dextran sulfate, pharmaceutically acceptable salts of dextran sulfate, hyaluronic acid and a pharmaceutically acceptable salts of hyaluronic acid.

6 Claims, No Drawings

CONDOM

BACKGROUND OF THE INVENTION

1. Field of the invention

The present invention relates to improved condoms, which are intended for use in covering the penis to prevent conception or infection.

Conventionally, there have been known condoms being provided with a coating layer of a jelly preparation mainly comprising silicone oil, glycerol and gelatine or a lubricant consisting principally of polyhydric alcohols and polysaccharic alcohols, that can realize for example improved convenience in unwinding and reduced feeling of foreignness in wearing.

However, such conventional condoms, because of their stickiness or uncomfortableness caused by crystallization of jelly or lubricant components, do not always impart satisfactorily comfortable feeling of wearing, and have the disadvantage in terms of providing complete protection for wounded parts and mucosa or skin.

The present invention has as its object to provide the condoms with enhanced degrees of safety and utility which have the above described disadvantage completely eliminated.

2. Description of related art

Dextran sulfates are used for treatment of scrapie (J. gen. Virol. 65, 423–428, 1984; Ibid, 65, 1325–1330 and Funkt. Biol. Med., 4, 129, 1985), and are also known to have pharmacological activity similar to heparin (Brit. Jour. Pharmacol., 7, 370, 1952; ibid, 8, 340, 1952; ibid, 9, 1, 1954, and Biochem., 51, 129, 1952). Dextran sulfates with lower moleular weights have long been commercialized as an antilipemic or anti-arteriosclerotic agent, while those with relatively higher molecular weights are known to have an inhibitory action against herpes virus (European Patent Publication No. 0066379). Hyaluronic acid is used as a surgical aid in the ophthalmological field (The Merck Index, 10th Ed., Number 4654).

SUMMARY OF THE INVENTION

The present invention provides an improved condom, which has a coating of thick material comprising a polysaccharide selected from the group consisting of dexran sulfate, or its pharmaceutically acceptable salts and/or, hyaluronic acid or its pharmacuetically acceptable salts. The polysaccharide serves as a lubricant and also as a skin- or mucosa-protective material. The thick material includes viscous liquid and cream or grease-like substance and has usually a viscosity of 5–500 CPS and preferably of 10–300 CPS.

DESCRIPTION OF PREFERRED EMBODIMENTS

In the present invention, a polysaccharide selected from the group consisting of dextran sulfate, and its pharmaceutically acceptable salts, as well as hyaluronic acid and its pharmaceutically acceptable salts is applied onto either or both of inside and outside surfaces of a condom. The said polysaccharide is preferably present at least in the vicinity of the closed end of the said condom.

In one preferred embodiment, an aqueous solution containing a polysaccharide selected from a group consisting of dextran sulfate, its pharmaceutically acceptable salts, hyaluronic acid and its pharmaceutically acceptable salts, or a mixture of at least two thereof with other optional lubricant, is applied by means of a suitable technique such as dripping, brushing, spraying, etc. to form a coating entirely or partly on the surface of the condom, as the case may be, thereby permitting the protection of a condom which can be kept in mild moist state, has good sliding property, and is free from feeling of wearing or foreignness. Further, dextran sulfate, its salts, hyaluronic acid and its salts exert an effect of protecting the skin or mucosa; they can prevent roughening dermatitic change, reddening, etc. of skin or mucosa; and they have a protecting effect even on a wounded site or sensitive skin. Accordingly, it is possible to obtain a condom having a high or degree of safety. As dextran sulfates and their salts have excellent water retaining or holding property, furthermore the surface of condom coated with them can retain a moderate wet state.

The dextran sulfates to be used in the present invention usually have a molecular weight of 2,000–300,000 and a sulfur content of 5–22%, of which preferred is one having a molecular weight of 3,000–8,000 and a sulfur content of 10–20%. The dextran sulfate can be prepared by a conventional process, which may be exemplified as follows:

Chlorosulfonic acid is added dropwise to dry pyridine of 8–10 fold the volume with cooling, to which small amount of formamide and dextran (about ¼ by weight of chlorosulfonic acid) are added, followed by heating (at 55°–65° C.) under stirring. After the reaction conclusion, the solvent is removed, and the residue is purified by re-precipitation, dialysis, etc. to give dextran sulfate.

Hyaluronic acid occurs naturally in animals, such as umbilical cord, articular fluid, vitreous fluid of the eye, avian crown, etc., and commercially available one may be usable. Preferred hyaluronic acid has a molecular weight of 1,000,000 to 10,000,000 and an intrinsic viscosity of 2.0 to 48.

The Pharmaceutically acceptable salts of dextran sulfate and hyaluronic acid include the salts with inorganic bases (e.g., sodium salt, potassium salt, ammonium salt, etc.) and the salts with organic bases (e.g., diethanolamine salt, cyclohexylamine salt, amino acid salt, etc.). These are produced by conventional procedures. Preferred salts are dermatologically acceptable ones.

In the present invention, dextran sulfates or their salts and/or hyaluronic acid or its salts can be applied the surface of condom in the form of a suitably concentrated aqueous solution, and for example, the aqueous solution of 10–70% concentration can yield a suitable wet condition. In the present invention, alternatively, the polysaccharide may be applied in the form of a preparation containing, in addition to the polysaccharide, other wetting materials.

As the other wetting materials, there can be used the water-soluble materials such as glycerin, glycols (e.g., propylene glycol, diethylene glycol, etc.), polyglycol, polyvinylalcohol, arginic acid or pharmaceutically acceptable salts thereof, carboxymethyl cellulose, gelatin, other saccharides, sodium chloride, sugar alcohols (e.g., maltitol, sobitol, etc.). The kind and amount of said other wetting materials vary depending on the desired effect and workability to be provided to the condom surface. By these materials it is possible to adjust the viscosity of the aqueous solution of the said polysaccharide, so as to provide more improved wet coating for a condom. Further, it is possible to incorporate a fat-soluble material, e.g., silicone oil into the solution. By homogenizing the silicone oil with the aqueous solution of the said polysaccharide by means of a homogenizer, there can be obtained a stable emulsion preparation, which may be conveniently applied on the condom surface. The amount to be applied per condom of the said polysaccharide is 0.001 mg–1,000 mg, preferably 0.01 mg–1,00 mg.

The coated condom obtained by the present invention has an effect of protecting the skin and mucosa. Thus, by providing the outer surface as well as the inner surface of the condom with a liquid film comprising the said polysaccharide according to the invention, it becomes possible to protect not only the skin and mucosa in contact of the male subject but also those of the female subject. The following non-limiting Examples illustrate the invention.

Example 1

A condom was prepared according to a conventional procedure and rolled in an annular form, and an aqueous solution of 60% sodium dextran sulfate (viscosity: 100 CPS) was added dropwise to the inside of the peripheral part thereof. The solution gradually permeated to spread uniformly over the whole surface of the condom to give a comfortably moist and supple coated condom.

The sodium dextran sulfate used here had a molecular weight of 7,000–8,000 and a sulfur content of 17–20%.

Example 2

Except that a solution comprising 1 g of sodium dextran sulfate, 50 g of glycerin, and 49 g of water (viscosity: 10 CPS) was used, the procedure in Example 1 was repeated to give a comfortably moist, and supple coated condom.

The sodium dextran sulfate used here had a molecular weight of 5,000–6,000 and a sulfur content of 13–15%.

Example 3

Except that a solution comprising 5 g of sodium dextran sulfate and 95 g of 70% maltitol (viscosity, 230 CPS) was used, the procedure in Example 1 was repeated to give a comfortably moist and supple coated condom.

The sodium dextran sulfate used here had a molecular weight of 3,000–4,000 and a sulfur content of 5–7%.

Example 4

Except that a solution comprising 1 g of hyaluronic acid and 99 g of 70% maltitol (viscosity: 250 CPS) was used, the procedure in Example 1 was repeated to give a comfortably moist and supple coated condom.

The hyaluronic acid used was of one having an average molecular weight of 1,000,000.

Comparative Example 1

A conventional condom was rolled in in an annular form without applying a wetting agent.

Comparative Example 2

Except that a silicone oil (viscosity: 100 CPS) was used, the procedure in Example 1 was repeated to give a wet condom.

Experiment 1

The condoms obtained in Example 1, Comparative Example 1 and Comparative Example 2 were used respectively by 20 healthy male subjects for 1 week at the rate of once a day, and feeling of wearing, feeling of foreigness, and effect on skin were evaluated.

The results are shown in the following Table.

| Feeling of wearing | Very comfortable | Comfortable | Ordinary | Uncomfortable | Very uncomfortable |
|---|---|---|---|---|---|
| Example 1 | 13/20 | 6/20 | 1/20 | 0/20 | 0/20 |
| Comparative Example 1 | 0/20 | 0/20 | 0/20 | 2/20 | 18/20 |
| Comparative Example 2 | 6/20 | 8/20 | 4/20 | 2/20 | 9/20 |
| Feeling of foreigness | None | Scarcely positive | Slightly positive | Positive | |
| Example 1 | 12/20 | 8/20 | 0/20 | 0/20 | |
| Comparative Example 1 | 0/20 | 0/20 | 1/20 | 19/20 | |
| Comparative Example 2 | 5/20 | 12/20 | 3/20 | 0/20 | |
| Effect on skin (1 week later) | Normal | Skin roughening | Dermatitic change | Reddening | |
| Example 1 | 20/20 | 0/20 | 0/20 | 0/20 | |
| Comparative Example 1 | 2/20 | 10/20 | 7/20 | 1/20 | |
| Comparative Example 2 | 9/20 | 8/20 | 3/20 | 0/20 | |

What is claimed is:

1. A condom having a coating of thick material, in which the thick material has a viscosity of 5–500 cps, comprising a polysaccharide selected from the group consisting of dextran sulfate, pharmaceutically acceptable salts of dextran sulfate, hyaluronic acid and a pharmaceutically acceptable salts of hyaluronic acid.

2. The condom of claim 1, in which the said polysaccharide is present at least in the vicinity of the closed end of the said condom.

3. The condom according to claim 1, in which the said dextran sulfate has a molecular weight of 500 to 2,000,000.

4. The condom according to claim 1, in which the said dextran sulfate has a sulfur content of 5 to 23%.

5. The condom according to claim 1, in which the said hyaluronic acid has a molecular weight of 1,000,000 to 10,000,000.

6. The condom according to claim 1, in which the said hyaluronic acid has an intrinisic viscosity of 2.0 to 48.

* * * * *